United States Patent [19]

Koch et al.

[11] Patent Number: 4,846,783

[45] Date of Patent: Jul. 11, 1989

[54] INCUBATOR FOR INFANTS

[75] Inventors: Jochim Koch, Hollenbeck; Michael Geier; Wolfgang Franz, both of Lübeck, all of Fed. Rep. of Germany

[73] Assignee: Drägerwerk Aktiengesellschaft, Lübeck, Fed. Rep. of Germany

[21] Appl. No.: 22,253

[22] Filed: Mar. 5, 1987

[30] Foreign Application Priority Data

Mar. 7, 1986 [DE] Fed. Rep. of Germany ....... 3607575

[51] Int. Cl.[4] .............................................. A61B 19/00
[52] U.S. Cl. ....................................................... 600/22
[58] Field of Search .................... 128/1 B, 1R; 98/36, 98/115.3, 31.5, 31.6; 600/21, 22

[56] References Cited

U.S. PATENT DOCUMENTS

| | | | |
|---|---|---|---|
| 2,633,842 | 4/1953 | Higgs | 128/1 B |
| 2,862,307 | 12/1958 | Bloomer et al. | 128/1 B |
| 3,051,163 | 8/1962 | Trexler | 128/1 B |
| 3,076,451 | 2/1963 | Stoner | 128/1 B |
| 3,134,243 | 5/1964 | Hagen et al. | 98/36 |
| 3,397,631 | 8/1968 | Simons | 98/36 |
| 4,361,137 | 11/1982 | Grosholz | 128/1 B |
| 4,509,505 | 4/1985 | Mercey et al. | 128/1 B |
| 4,566,293 | 1/1986 | Arner et al. | 128/1 B |

FOREIGN PATENT DOCUMENTS

| | | | |
|---|---|---|---|
| 1232048 | 5/1971 | Fed. Rep. of Germany | 128/1 B |
| 1024663 | 9/1950 | France | 128/1 B |
| 1057307 | 5/1952 | France | 128/1 B |

OTHER PUBLICATIONS

Hey and Mount, Heat Losses from Babies in Incubators, 1967, pp. 79–82.

*Primary Examiner*—Edward M. Coven
*Assistant Examiner*—J. P. Lacyk
*Attorney, Agent, or Firm*—Walter Ottesen

[57] ABSTRACT

An incubator for maintaining a warm environment for infants includes a substantially elongated resting or bed surface which is surrounded by a hood. At least one side wall of the front side has closable access openings. An air outlet for supplying air into the hood and an air inlet for carrying air away from the hood are provided at the peripheral region of the resting surface. In the incubator, the air is guided to maintain a stable incubator air temperature to reduce heat losses from convection and radiation with the hood closed and, with the front side opened, the buildup of a stable warm-air curtain is promoted. For this purpose, the air outlet is disposed along the front side, and the air inlet is disposed along the rear side opposite this front side.

7 Claims, 2 Drawing Sheets

INCUBATOR FOR INFANTS

FIELD OF THE INVENTION

The invention relates to an incubator for maintaining a warm environment for infants. The incubator includes a substantially elongated resting or bed surface enclosed by a hood. At least one side wall of the hood is configured as a front side having closable access openings. In the periphery of the resting surface, there is an air outlet for supplying air into the hood and an air inlet for carrying air away from the hood.

BACKGROUND OF THE INVENTION

Incubators of this type are used for receiving infants as well as prematures and newborns to isolate them in a protected atmosphere. The incubator air should be adjustable within certain limits in terms of temperature, oxygen content and humidity, and it should be possible to maintain these quantities within these limits. In particular, especially stringent requirements are made for temperature stability and uniform distribution of temperature in the vicinity of the resting surface. This is true both when the incubator is closed and during necessary treatment procedures to be performed on the patient. During such treatment, the openings provided for this purpose, such as access openings or relatively large flaps, have to be opened. The heat supplied to the interior of the incubator then should not escape into the colder ambient to more than the minimum possible extent and, even in the closed state, heat loss due to convection or radiant heat should be as low as possible.

Published German patent application DE-OS No. 31 00 932, discloses an incubator having a rectangularly shaped resting surface inside a hood, at the head and foot ends of which an air outlet and air inlet, respectively, are provided. Warmed air is blown from the air outlet into the hood interior via a recirculating apparatus and aspirated at the foot end via the air inlet. The circulating warm air is distributed in the bed region, where it should maintain a constant temperature. On the long side of the hood, there is a relatively large flap provided with manual access openings, which can be vertically opened and pivoted entirely out of the way. With the front flap opened, an additional air outlet for the warmed incubator air is made available, and this air outlet extends all the way along the long side of the resting surface. The warm incubator air now escapes at the head end as well as at the newly opened air outlet along the long side of the front flap, and is aspirated away via the remaining air inlet at the foot end.

In this known incubator, with the front flap opened, a warm-air curtain is to be provided which is intended to prevent an exchange of air with the ambient. This kind of air curtain, however, is only incompletely attained by means of the known warm-air guidance because warm air is now being blown out of two air outlet openings, the flow paths of which intersect in opposite directions, so that a closed circulation of air between the two air outlets and the single air inlet on the foot end can no longer take place. Instead, an aspiration of unwanted air takes place through the opened front flap, and a corresponding expulsion of warm air takes place out of the incubator interior. The result is an appreciable disruption of the temperature equilibrium in the incubator interior, and there is a considerable change in the temperature level in the vicinity of the resting surface.

Even with the front panel closed (and thus without the air curtain on the front side), the known air guidance does not produce the desired reduction of the heat loss of the infant from radiant heat. The outflowing warm air heats only the end faces of the incubator hood, which have a relatively small surface area, while in contrast, a considerable radiant heat loss continues to take place through the front and rear sides of the hood, which have a large surface area and are colder.

If the front side is closed and the manual access openings located therein are opened, then the front air outlet remains closed, and no warm-air curtain forms, so that cold air can enter from the ambient into the incubator interior.

Published European patent application No. 0 032 133 discloses an incubator having a cylindrically-shaped double-walled hood, which is divided into segments along the cylinder axis. With the hood closed, the warm air is blown via an air outlet at the rear side of the hood into the intermediate space of the double wall and then reaspirated out of the intermediate space at the front side. A plurality of openings in the inner shell of the double-walled hood allow a small portion of the warm air to enter into the interior of the hood. With the front side opened, the air circulation between the hood shells is interrupted, so that all the warm air is blown in via the openings in the inner shell into the interior of the hood. Since the air inlet along the front side is now completely opened with respect to the ambient, not only the warm incubator air but cold ambient air as well as aspirated, and a large proportion of the incubator air escapes into the cold ambient. Here again, a drop in the incubator temperature occurs which leads to considerable convection heat loss for the patient in the incubator. If the front side is opened completely, all the warmed incubator air escapes to the ambient, and maintenance of the previously adjusted air temperature is no longer assured.

SUMMARY OF THE INVENTION

It is an object of the invention to provide an incubator wherein the conduction of air in order to maintain a stable incubator air temperature with the hood closed reduces heat losses from convection and radiation, and with the front side partially or fully open, the conduction of air promotes the buildup of a stable warm-air curtain.

According to a feature of the invention, the above object is attained by placing the air outlet along the front side of the incubator and the air inlet along the rear side opposite the air outlet.

The advantage of the invention is substantially that by means of the air outlet and air inlet which are configured so as to extend along the long sides of the incubator, a substantial reduction in the airflow velocity can be attained, so that inside the incubator, at the location where the patient is lying, as little air turbulence as possible occurs, so that there is little heat loss caused by air convection. Nevertheless, the air quantity required for stable air temperature regulation can still be circulated to a sufficient extent. Even with the access openings on the front wall opened, only a very small heat loss occurs because the air curtain along the closed front side rises on the inside and is aspirated away by the air inlet on the rear side of the incubator.

Even with the front side opened completely, a self-contained air circulation continues to be maintained in the incubator interior, and the aspiration of unwanted air from the ambient is of no significance for maintaining a stable air temperature in the incubator interior. Furthermore, a mechanically complicated control mechanism for rerouting the guided air when the front flap is opened is completely obviated.

To further increase the thermal isolation of the incubator interior with respect to the ambient, the front side and rear side of the incubator can be configured as respective double walls. Each of the double walls defines an interspace opening at the upper end and the air outlet and air inlet communicate with respective ones of the intermediate spaces of the double walls. This provides a directed air flow curtain which moves inside the intermediate spaces of the double walls and thus generates a heating insulation layer at the wall portions of the incubator hood that have a large surface area.

According to a further feature of the invention, the peripheral region of the double wall is left open only on the end thereof opposite the air outlet or air inlet. This provides a still more accurately directed alignment of the airflow in the interspace of the double wall and the circulating air is guided substantially along the hood, while the area where the infant lies is now located in a zone of calmed flow.

In order to attain a constant airflow extending uniformly along the air outlet, guide ribs are provided at the air outlet. These guide ribs provide that at every point along the air outlet, the warmed incubator air sweeps along the inside surface of the front side and is directed vertically upwardly with the same flow speed, or with the front flap opened, the warmed air flows freely vertically upwardly thereby forming a stable warm-air curtain.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
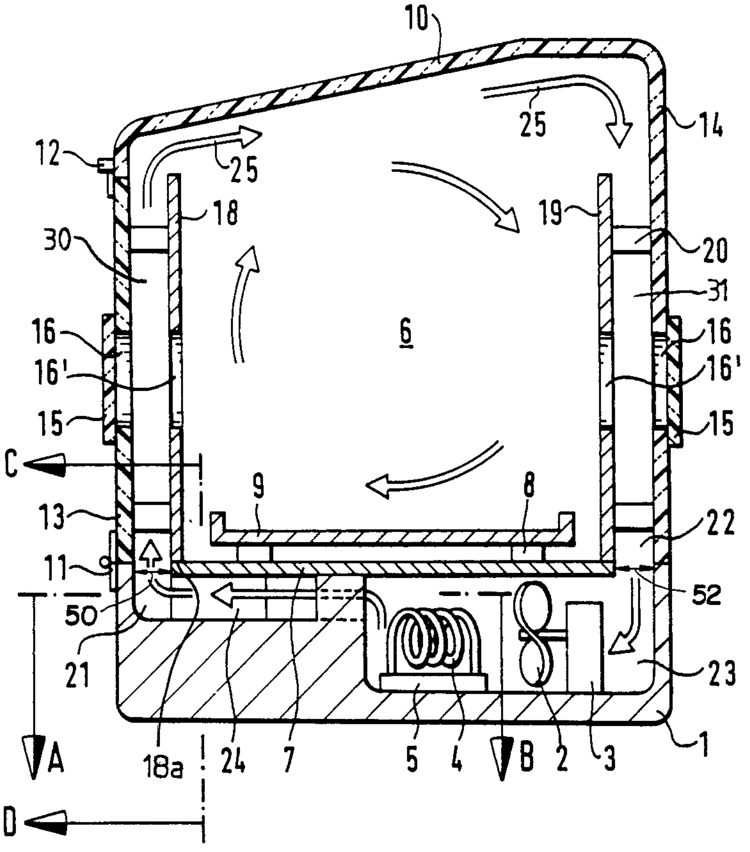
FIG. 1 shows the incubator according to the invention in section.

The incubator of FIG. 1 has a base 1 for receiving various equipment of which the fan 2 with its drive motor 3 and the heater 4 with its supply unit 5 are shown. The base 1 is separated from the incubator interior 6 by a resting surface 7 in the form of an elongated supporting member. The resting surface 7 has two longitudinally extending sides and supports a cot 9 via posts 8 for receiving the infant (not shown). The interior 6 is closed off from the ambient with a hood 10 that is transparent on all sides. A front flap 13 is located on the front wall of the hood 10 and is retained via hinges 11 and latches 12. This front flap can be opened fully downward by pivoting about its hinges 11. Access openings 16 that are closable with flaps 15 are located both in the front flap 13 and on the rear wall 14 of the hood 10.

Spaced slightly apart from the inside surfaces of the front flap 13 and the rear wall 14 are first and second ancillary walls (18, 19), which also have access openings 16' opposite the access openings 16. The ancillary walls 18, 19 are joined via spacers 20 to the front flap 13 and rear wall 14, respectively. When the front flap 13 is opened, the second wall 18 is pivoted as well so that there is a separable interface at **18*a*. The air outlet 21 is located between the longitudinally extending end of the resting surface 7 and the front wall of the incubator provided with the front flap 13. The pass-through opening between this longitudinally extending end and the front wall is identified in FIG. 1 by the double arrow 50. The air inlet 22 is located on the rear side of the incubator between the rear wall 14 and the resting surface 7 and the pass-through opening is identified by the double arrow 52**.

During operation and with the incubator hood closed, the interior air is conducted via the air inlet 22 to the fan 2 into the guide channel 23. From there the interior air is moved along the heater 4 whereat the air is heated to the desired temperature. After the heater 4, the heated air leaves the air outlet 21 and enters the incubator interior 6. In so doing, the heated air is distributed uniformly along the air outlet 21 via guide ribs 24 and guided vertically upwardly. The airflow along the front wall having the front flap 13 and from the intermediate space 30 between the front flap 13 and the ancillary wall 18 on the one hand, and along the rear wall 14 and into the intermediate space 31 between the rear wall 14 and ancillary wall 19 on the other, is indicated by the arrows 25. During the through-flow of the heated air along the top wall of the hood 10, a slight turbulence is brought about in the warm air in the incubator interior, so that the heated air reaches the vicinity of the cot 9.

Figure 2:
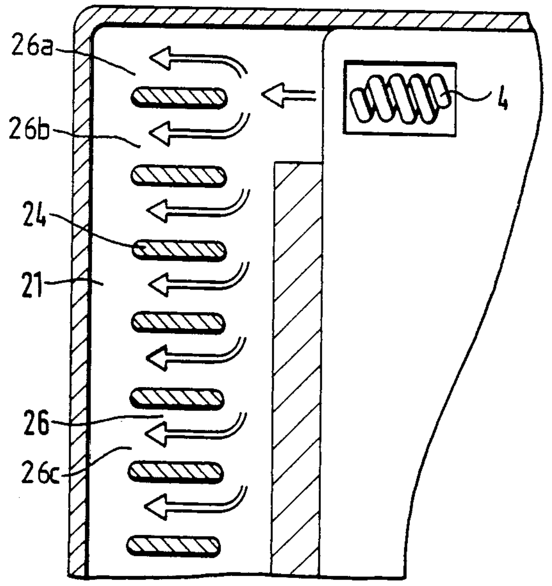
FIG. 2 is a partial plan view on the air outlet taken along the line A–B; and, FIG. 3 is a cross section through a portion of the air outlet taken along the line C–D.
Figure 3:
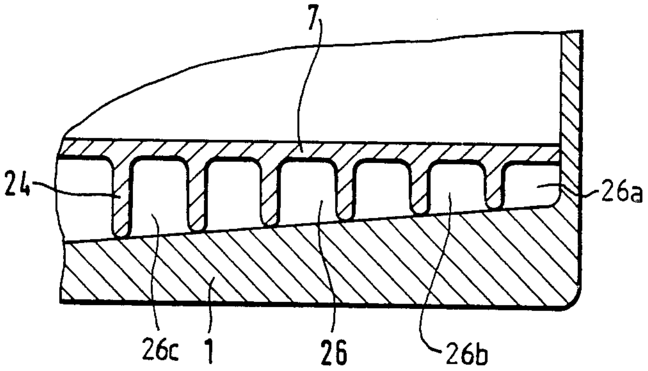

In FIGS. 2 and 3, a portion of the air outlet 21 is shown in different sectional views and on a larger scale.

The air moved by the fan 2 across the heater 4 is blown into the air outlet 21 through the channels 26 between the guide ribs 24. The arrangement of the guide ribs 24 is seleced to be such that the heated air flows into the air outlet 21 at a right angle. The cross sections of the respective channels 26 formed between the resting surface 7 and the base 1 are configured such that the heated air flows uniformly into the air outlet 21 in terms of its flow velocity and quantity. More specifically, the channels (**26*a*, 26*b*) are substantially in line with the blower 2 and so receive the moved air at a greater intensity of pressure than does channel 26*c*, for example, further down along the longitudinal length of the incubator. However, the cross section of channel 26*c* is considerably larger than the cross sections of channels 26*a* and 26*b* so that less resistance to the heated air is provided to air flowing through channel 26*c*. Accordingly, the flow of air entering air outlet 21 from the channels 26 and passing upwardly in the interspace 30** is uniform along the entire longitudinal length of the incubator.

Other embodiments are possible, for example, rather than moving the air into channels 26 from a blower 2 and heater 4 at one longitudial end of the incubator as shown above, the heater could be mounted, for example, at the longitudinal center of the incubator in which case the channels 26 of smallest cross section would also be disposed at the longitudial center of the incubator with channels of increasing cross section being disposed to the left and right of these channels of smaller cross section.

It is understood that the foregoing description is that of the preferred embodiments of the invention and that various changes and modifications may be made thereto without departing from the spirit and scope of the invention as defined in the appended claims.

What is claimed is:

1. An incubator for maintaining a warm environment for an infant, the incubator comprising:

a base;

an elongated supporting member defining a longitudinal axis and having upwardly facing surface means adapted to receive the infant thereon, said supporting member having first and second longitudinally-extending sides and being mounted on said base;

a hood mounted on said base so as to conjointly define the interior of the incubator therewith for accommodating said supporting member, said hood having a rear wall extending parallel to said axis and having a front wall likewise extending parallel to said axis and being provided with access openings and closable flaps for closing said access openings, said front and rear walls being disposed adjacent said first and second longitudinally-extending sides, respectively;

air outlet means for passing air into said interior, said air outlet means extending only along the length of said front wall and defining an air outlet gap between said front wall and said first longitudinally-extending side of said supporting member;

air inlet means for passing air from said interior, said air inlet means extending only along the length of said rear wall and defining an air inlet gap between said rear wall and said second longitudially-extending side of said supporting member;

said air outlet means and said air inlet means extending along virtually the entire lengths of said front and rear walls, respectively, so as to permit the air to pass into said interior along the entire length of said front wall and to pass out of said interior along the entire length of said rear wall to thereby reduce air turbulence to a minimum at the region of the infant; and, blower means mounted in said base for moving the air between said air inlet means and said air outlet means.

2. An incubator for maintaining a warm environment for an infant, the incubator comprising:

a base;

an elongated supporting member defining a longitudinal axis and having upwardly facing surface means adapted to receive the infant thereon, said supporting member having first and second longitudinally-extending sides and being mounted on said base;

a hood mounted on said base so as to conjointly define the interior of the incubator therewith for accommodating said supporting member, said hood having a top wall and a rear wall extending downwardly from said top wall and parallel to said axis and having a front wall likewise extending downwardly from said top wall and parallel to said axis and being provided with access openings and closable flaps for closing said access openings, said front and rear walls being disposed adjacent said first and second longitudinally-extending sides, respectively;

air outlet means for passing air into said interior, said air outlet means extending along the length of said front wall and being disposed in the region between said front wall and said first longitudinally-extending side of said supporting member;

air inlet means for passing air from said interior, said air inlet means extending along the length of said rear wall and being disposed in the region between said rear wall and said second longitudinally-extending side of said supporting member;

said air outlet means and said air inlet means extending along virtually the entire lengths of said front and rear walls, respectively, so as to permit the air to pass into said interior along the length of said front wall and to pass out of said interior along the length of said rear wall to thereby reduce air turbulence to a minimum at the region of the infant;

blower mounted in said base means for moving the air between said air inlet means and said air outlet means; and, said air outlet means including: a first ancillary wall adjacent the inside surface of said front wall to conjointly define a first intermediate space therebetween and said first intermediate space extending upwardly to just beneath said top wall so as to direct the flow of air thereagainst; and, said front wall and said first longitudinally-extending side conjointly defining an air outlet opening disposed along the entire length of said front wall so as to communicate with said first intermediate space; and, said air inlet means including: a second ancillary wall adjacent the inside surface of said rear wall to conjointly define a second intermediate space therebetween and said second intermediate space extending downwardly from just beneath said top wall for conducting air away from said interior; and, said rear wall and said second longitudinally-extending side conjointly defining an air inlet opening disposed along the entire length of said rear wall so as to communicate with said second intermediate space.

3. The incubator of claim 2, said ancillary walls having respective peripheral edges and said intermediate spaces communicating with said interior at corresponding ones of said peripheral edges.

4. The incubator of claim 1, said air outlet means including: a first ancillary wall adjacent the inside surface of said front wall to conjointly define a first intermediate space therebetween, said first ancillary wall having lateral edges and top and bottom edges and being mounted on said front wall so as to cause said first intermediate space to communicate with said interior only at said top edge; and, said front wall and said first longitudinally-extending side conjointly defining an air outlet opening disposed along the length of said front wall so as to communicate with said first intermediate space at said bottom edge; and, said air inlet means including a second ancillary wall adjacent the inside surface of said rear wall to conjointly define a second intermediate space therebetween, said second ancillary wall having lateral edges and top and bottom edges and being mounted on said rear wall so as to cause said second intermediate space to communicate with said interior only at said top edge of said second ancillary wall; and, said rear wall and said second longitudinally-extending side conjointly defining an air inlet opening disposed along the length of said rear wall so as to communicate with said second intermediate space at said bottom edge of said second ancillary wall.

5. The incubator of claim 1, comprising heater and guide means for directing warmed air toward said air outlet mounted in said base; and, a plurality of channels interposed between said heater and guide means and said air outlet for channelling the heated air to said air outlet.

6. An incubator for maintaining a warm environment for an infant, the incubator comprising:

a base;

an elongated supporting member defining a longitudinal axis and having upwardly facing surface means adapted to receive the infant thereon, said supporting member having first and second longitudinally-extending sides and being mounted on said base;

a hood mounted on said base so as to conjointly define the interior of the incubator therewith for accommodating said supporting member, said hood having a rear wall extending parallel to said axis and having a front wall likewise extending parallel to said axis and being provided with access openings and closable flaps for closing said access openings, said front and rear walls being disposed adjacent said first and second longitudinally-extending sides, respectively;

air outlet means for passing air into said interior, said air outlet means extending only along the length of said front wall and defining an air outlet gap between said front wall and said first longitudinally-extending side of said supporting member;

air inlet means for passing air from said interior, said air inlet means extending only along the length of said rear wall and defining an air inlet gap between said rear wall and said second longitudinally-extending side of said supporting member;

said air outlet means and said air inlet means extending along virtually the entire lengths of said front and rear walls, respectively, so as to permit the air to pass into said interior along the entire length of said front wall and to pass out of said interior along the entire length of said rear wall to thereby reduce air turbulence to a minimum at the region of the infant;

blower means mounted in said base for moving the air between said air inlet means and said air outlet means;

heater and guide means for directing warmed air toward said air outlet mounted in said base; and, a plurality of channels interposed between said heater and guide means and said air outlet for channelling the heated air to said air outlet; and, said channels having respective cross sections which increase in area with increasing distance from said heater and guide means thereby providing a uniform flow distribution into said first intermediate space.

7. An incubator for maintaining a warm environment for an infant, the incubator comprising:

a base;

an elongated supporting member defining a longitudinal axis and having upwardly facing surface means adapted to receive the infant thereon, said supporting member having first and second longitudinally-extending sides and being mounted on said base;

a hood mounted on said base so as to conjointly define the interior of the incubator therewith for accommodating said supporting member, said hood having a rear wall extending parallel to said axis and having a front wall likewise extending parallel to said axis and being provided with access openings and closable flaps for closing said access openings, said front and rear walls being disposed adjacent said first and second longitudinally-extending sides, respectively;

air outlet means for passing air into said interior, said air outlet means extending only along the length of one of said walls and defining an air outlet gap between said one wall and the longitudially-extending side of said supporting member;

air inlet means for passing air from said interior, said air inlet means extending only along the length of the other one of said walls and defining an air inlet gap between said other wall and the other longitudinally-extending side of said supporting member;

said air outlet means and said air inlet means extending along virtually the entire lengths of said walls, respectively, so as to permit the air to pass into said interior along the entire length of said one wall and to pass out of said interior along the entire length of said other wall to thereby reduce air turbulence to a minimum at the region of the infant; and, blower means mounted in said base for moving the air between said air inlet means and said air outlet means.

* * * * *

UNITED STATES PATENT AND TRADEMARK OFFICE
CERTIFICATE OF CORRECTION

PATENT NO. : 4,846,783

DATED : July 11, 1989

INVENTOR(S) : Jochim Koch, Michael Geier and Wolfgang Franz

It is certified that error appears in the above-identified patent and that said Letters Patent is hereby corrected as shown below:

In column 2, line 32: delete "as", second occurrence, and substitute -- is -- therefor.

In column 4, line 58: delete "longitudial" and substitute -- longitudinal -- therefor.

In column 4, line 62: delete "longitudial" and substitute -- longitudinal -- therefor.

In column 6, line 13: insert -- means -- between "blower" and "mounted".

In column 6, line 13: delete "means" between "base" and "for".

In column 8, line 29: delete "longitudially-" and substitute -- longitudinally -- therefor.

Signed and Sealed this

Tenth Day of March, 1992

*Attest:*

HARRY F. MANBECK, JR.

*Attesting Officer*

*Commissioner of Patents and Trademarks*